(12) United States Patent
Rosenfeld et al.

(10) Patent No.: US 6,667,308 B2
(45) Date of Patent: Dec. 23, 2003

(54) COMPOUNDS FOR USE AS ANTIDEPRESSANTS, APHRODISIACS AND ADJUNCTIVE THERAPIES IN HUMANS

(75) Inventors: Mark J. Rosenfeld, Holladay, UT (US); Patricia J. Berger, Cora, WY (US); Norman C. Negus, Cora, WY (US)

(73) Assignee: Seroctin Research & Technology, Inc., Salt Lake City, UT (US)

( * ) Notice: Subject to any disclaimer, the term of this patent is extended or adjusted under 35 U.S.C. 154(b) by 0 days.

(21) Appl. No.: 09/834,592

(22) Filed: Apr. 13, 2001

(65) Prior Publication Data

US 2001/0053789 A1 Dec. 20, 2001

Related U.S. Application Data

(60) Provisional application No. 60/196,829, filed on Apr. 13, 2000.

(51) Int. Cl.[7] .................. A61K 31/428; A61K 31/538
(52) U.S. Cl. ..................... 514/230.5; 514/375
(58) Field of Search ............... 514/375, 376, 514/230.5; 548/221, 217

(56) References Cited

U.S. PATENT DOCUMENTS

| | | | | |
|---|---|---|---|---|
| 5,240,919 | A | 8/1993 | Yous et al. | 514/210 |
| 5,300,507 | A | 4/1994 | Yous et al. | 514/253 |
| 5,322,843 | A | 6/1994 | Yous et al. | 514/233.8 |
| 5,322,849 | A | 6/1994 | Yous et al. | 514/321 |
| 5,326,775 | A | 7/1994 | Yous et al. | 514/375 |
| 5,386,034 | A | 1/1995 | Yous et al. | 548/169 |
| 5,436,348 | A | 7/1995 | Yous et al. | 548/221 |

FOREIGN PATENT DOCUMENTS

| | | | | |
|---|---|---|---|---|
| CH | 683593 | 4/1994 | ......... | A61K/31/535 |
| EP | 0 506 539 | 9/1992 | ......... | C07D/263/58 |

OTHER PUBLICATIONS

Pischon et al;PuBMed Abstr. 12187313; Curr Opin Nephrol Hypertens; Recent dev. in treat. of obesity, 11/5, 497–502(2002).*
Garcia H.L.;PubMed Abstr. 12180897;Am J. Clin. Dermat.; Dermatological Complications, 3/7,497–506(2002).*
Wang et al;PubMed Abstr. 10752670;Pharm. Toxicol,Hypotensive activity of the pineal . . . , 86/3, 125–8(2000).*
Lee HS;Pubmed Abstr. 11879010;J Agric Food Chem; Tyrosinase inhibitors of . . . , 50/6, 1400–3(2002).*
Gower et al., "Reproductive responses of male *Microtus montanus* to photoperiod . . . ", *Journal of Pineal Research*, 8:297–312, 1990.
Sweat et al., "Uterotropic 6–methoxybenzoxazolinone . . . ", *Molecular and Cellular Endocrinology*, 57:131–138, 1988.
Daya et al., "Effect of 6–methoxy–2–benzoxazolinone on the activities of rat . . . ", *Journal of Pineal Research*, 8:57–66, 1990.
Anderson et al., "Effects of melatonin and 6–methoxybenzoxazolinone on photoperiodic control . . . ", *Journal of Pineal Research*, 5:351–65, 1988.
Yuwiler et al., "Effects of 6–methoxy–2–benzoxazolinone on the pineal melatonin . . . ", *J. Pharmacol. Exp. Ther.*, 233:45–50, 1985.
Gower, "Endocrine effects of the naturally occuring reproductive stimulant . . . ", Ph.D. Thesis, University of Utah, Salt Lake City, UT, 116 pp. 1990.
Butterstein et al., "The plant metabolite 6–methoxybenzoxazolinone interacts . . . ", *Biology of Reproduction*, 39:465–71, 1988.
Vaughan et al., "Hormonal consequences of subcutaneous 6–methoxy–2–benzoxazolinone . . . ", *Journal of Reproduction and Fertility* 83:859–66, 1988.
Urbanski et al., "Influence of photoperiod and 6–methoxybenzoxazolinone on the reproductive axis . . . " *Journal of Reproduction and Fertility* 90:157–162, 1990.
Bjostad, Louis B. and Hibbard, Bruce E., "6–Methoxy–2–Benzoxazolinone: A Semiochemical for Host Location by Western Corn Rootworm Larvae," Journal of Chemical Ecology, vol. 18, No. 7, pp. 931–944, 1992.
Mayoral, Ana M. et al. "A High Performance Liquid Chromatography Method for Quantification of DIBOA, DIMBOA, and MBOA from Aqueous Extracts of Corn and Winter Cereal Plants," Journal Of Liquid Chromatography, vol. 17, No. 12, pp. 2651–2665, 1994.

* cited by examiner

*Primary Examiner*—John M. Ford
(74) *Attorney, Agent, or Firm*—Pate Pierce & Baird (57) ABSTRACT

Phenolic compounds with a phenolic molecule to which are covalently linked an oxygen-containing group, a nitrogen- or another oxygen containing group, and a $C_1$–$C_4$ alkoxy group, obtainable from monocotyledonous plants, animals that eat such plants, or chemical synthesis, have been found to act as an antidepressant or otherwise a treatment for bettering mood, a therapy for improving sexual desire or performance, an adjunctive therapy for achieving weight loss, and an adjunctive therapy for substance abuse and addiction. These compounds, at concentrations suitable for human therapeutic use, may be obtained from plants such as corn in their early growth stages and from parts of animals such as the velvet antler tips of deer and elk.

52 Claims, 8 Drawing Sheets

FIG. 1. Generalized chemical structures and parameters defining the compounds of invention.

---

Formula I -- A compound according to the formula

Wherein "R" represents $C_1$-$C_4$ alkoxy, with the proviso that R is in the 4 or 5 ring position;

Wherein "n" represents one of the integers 0, 1 or 2;

Wherein "A" represents -OH, -$NH_2$, or NHCR', where R' represents $C_1$-$C_4$ alkyl;

Or a pharmaceutically acceptable salt thereof..

Formula II -- A compound according to the formula

Wherein "R" represents $C_1$-$C_4$ alkoxy, with the proviso that R is in the 5 or 6 ring position;

Wherein "n" represents one of the integer 0, 1 or 2;

Or a pharmaceutically acceptable salt thereof..

FIG. 1. Continued.

Formula III -- A compound according to the formula

Wherein "R" represents $C_1$-$C_4$ alkoxy, with the proviso that R is in the 6 or 7 ring position;

Wherein "n" represents one of the integer 0, 1 or 2;

Or a pharmaceutically acceptable salt thereof..

FIG. 2. Chemical structures for representative members of Formulas I, II and III. That members of Formulas I, II and III have similar effects on vertebrates is evidenced by Example 1. Such forms a foundation for members of Formulas I, II and III to be collectively unified as compounds of invention.

---

1. 2-amino-5-methoxyphenol [Member of Formula I]

2. 6-methoxy-2-benzoxazolinone [Member of Formula II]

3. 2,4-dihydroxy-7-methoxy-1,4-(2H)-benzoxazin-3-one [Member of Formula III]

FIG. 2. Continued.

4. 2-hydroxy-4-methoxyacetanilide [Member of Formula I]

5. 2-hydroxy-4-ethoxyacetanilide [Member of Formula I]

6. 5-methoxy-2-benzoxazolinone [Member of Formula III]

7. 2-hydroxy-5-methoxyacetanilide [Member of Formula I]

FIG. 3. Effect of injecting compounds of invention, members of Formulas I, II and III as defined in FIG. 1 and FIG. 2, intraperitoneally for 3 consecutive days and sacrificing 24 hours after the last injection on uterine weight in the montane vole, Microtus montanus. The results indicate similar physiological responses for compounds belonging to the compounds of invention. "Formula Numeral" refers to the formula categories specified in FIG. 1. Average uterine weight is in milligrams.

| Compound Injected | Formula Numeral | Number of Animals | Average Uterine Weight |
| --- | --- | --- | --- |
| Control (Propylene Glycol) | --- | 8 | 15.2 ± 2.4 |
| 6-methoxy-2-benzoazolinone | II | 11 | 27.7 ± 5.6 * |
| 5-methoxy-2-benzoxazolinone | III | 8 | 20.0 ± 4.7 ** |
| 2-hydroxy-4-methoxyacetanilide | I | 8 | 23.1 ± 2.7 * |
| 2-hydroxy-4-ethoxyacetanilide | I | 8 | 22.2 ± 3.9 * |
| 2-amino-5-methoxyphenol | I | 8 | 21.8 ± 3.5 * |
| 2-hydroxy-5-methoxyacetanilide | I | 8 | 21.1 ± 4.4 *** |
| 2-amino-4-methoxyphenol | I | 8 | 22.2 ± 3.2 * |

\* Significantly different from control at $P < 0.001$

\*\* Significantly different from control at $P = 0.015$

\*\*\* Significantly different from control at $P = 0.004$

FIG. 4. HAD and ASEX summaries for administration of the compounds of invention to adult males. The HAD value precedes the ASEX one, and these are separated from each other by a comma. Compounds of invention had a significant positive effect on depression or feelings of well-being.

| Participant | With Compounds of Invention: Initial Value | With Compounds of Invention: After Two-Weeks | With Placebo: Initial Value | With Placebo: After Two-Weeks |
|---|---|---|---|---|
| 1 | 9.0, 12.0 | 8.0, 11.0 | 8.0, 10.0 | 8.0, 13.0 |
| 2 | 16.0, 13.0 | 14.0, 12.0 | 16.0, 13.0 | 16.0, 15.0 |
| 3 | 15.0, 10.0 | 9.0, 11.0 | 15.0, 14.0 | 17.0, 14.0 |
| 4 | 12.0, 9.0 | 7.0, 10.0 | 9.0, 10.0 | 9.0, 12.0 |
| 5 | 14.0, 10.0 | 10.0, 10.0 | 12.0, 10.0 | 14.0, 10.0 |
| 6 | Participant not reliable -- Data incomplete and deleted from study | | | |
| 7 | 12.0, 9.0 | 7.0, 9.0 | 9.0, 10.0 | 8.0, 9.0 |
| 8 | 12.0, 11.0 | 8.0, 11.0 | 12.0, 11.0 | 12.0, 10.0 |
| 9 | 12.0, 15.0 | 12.0, 10.0 | 7.0, 10.0 | 7.0, 10.0 |
| 10 | 4.0, 15.0 | 0.0, 13.0 | 9.0, 12.0 | 12.0, 12.0 |
| 11 | 21.0, 10.0 | 6.0, 10.0 | 9.0, 12.0 | 12.0, 12.0 |
| 12 | 13.0, 9.0 | 2.0, 9.0 | 13.0, 9.0 | 13.0, 9.0 |
| 13 | 14.0, 12.0 | 13.0, 10.0 | 12.0, 10.0 | 12.0, 10.0 |
| 14 | 12.0, 10.0 | 13.0, 10.0 | 18.0, 7.0 | 16.0, 7.0 |
| 15 | 23.0, 8.0 | 18.0, 9.0 | 16.0, 9.0 | 16.0, 8.0 |
| Average | 13.5, 10.9 | 9.1, 10.4 | 11.8, 10.5 | 12.3, 10.8 |

Two-Sample Paired Sign Test -- This is one of the stronger or more reliable statistical tests when significance is detected. The question is whether INVENTION affects feelings of well-being or sexual function. The Sign-Test is used to statistically ask "how often compounds of invention impacts feelings of well being and/or sexual function". Results are as follows:

HAD (with invention), $p < 0.003$, Very Significant          ASEX (with invention), $p < 0.727$, Not Significant
HAD (with placebo), $p < 0.688$, Not Significant          ASEX (with placebo), $p < 1.310$, Not Significant FIG. 5. HAD summary for clinically-depressed females taking compounds of invention for six weeks. HAD values were ascertained at the onset and end of the trial period. Note that all participants had HAD scores at the onset verifying clinical depression. Only two females scored as clinically depressed after six weeks. Albeit few people in the trial, compounds of invention still had a significant positive effect on lessening depression.

| Participant[1] | Initial Value | After Six-Weeks |
|---|---|---|
| 1 | 23.0 | 18.0 |
| 2 | 21.0 | 8.0 |
| 3 | 21.0 | 21.0 |
| 4 | 24.0 | 14.0 |
| 5 | 22.0 | 12.0 |
| 6 | 21.0 | 13.0 |
| 7 | 23.0 | 7.0 |
| 8 | 20.0 | 22.0 |
| Average | 21.9 | 14.4 |

HAD, $p < 0.0313$, Significant

[1] Participants 1-4 initially [Weeks 1-2] were given compounds of invention under the guise of its being a vitamin / mineral mixture.

Two-Sample Paired Sign Test — This is one of the stronger or more reliable statistical tests when significance is detected. The question is whether compounds of invention affect depression or feelings of well-being. The Sign-Test is being used to statistically ask "how often compounds of invention positively impact depression or feelings of well being". The result is as follows:

FIG. 6. 6-MBOA in Dried Velvet Antler from Elk, Cervus elaphus.

| Animal | Origin | Tip or Other | Drying Method | 6-MBOA (mg/g dry weight) |
|---|---|---|---|---|
| Wapiti | Canada | Tip | Air | 2.5 |
| Wapiti | Canada | Tip | Air | 2.8 |
| Wapiti | Canada | Other | Air | 0.3 |
| Red Deer | New Zealand | Tip | Freeze | 1.9 |
| Red Deer | New Zealand | Other | Freeze | 0.5 |

COMPOUNDS FOR USE AS ANTIDEPRESSANTS, APHRODISIACS AND ADJUNCTIVE THERAPIES IN HUMANS

RELATED APPLICATION

This application claims the benefit of provisional application Serial No. 60/196,829, filed Apr. 13, 2000, and entitled "An Antidepressant, Aphrodisiac, Weight-Loss Aid, Therapy for Quitting Nicotine or Addictive Drugs and Treatment for Bettering Reproduction in Humans."

BACKGROUND OF THE INVENTION

1. Field

The invention is in the field of treating depression, sexual dysfunction, substance abuse or addiction, and in inducing weight loss, compounds used in such treatments, and the making of such compounds.

2. State of the Art

An estimated 35–40 million living Americans will suffer major depressive episodes, and many more will experience lesser bouts. Of the approximately 17.5 million Americans with ongoing depressions, about 9.2 million are at a clinically debilitating level. Clinical depression is characterized by a list of symptoms that last over a long time span. It is a serious problem that is usually or initially caused by outside stressors. As stresses escalate or persist, a chemical imbalance can result. Clinical depression can be very debilitating both physically and mentally and even lead to death by means of suicide. However, lost productivity and relationship problems are also consequences of lesser depressions. At present, antidepressant medications are the cornerstones of treating depression, especially those that are at least moderately severe. Although depressed people tend to improve when treated with antidepressants, many do not respond to the first one. Such individuals may eventually benefit from a different antidepressant or a combination of antidepressants.

Sexual dysfunction is a pervasive disorder. In the overall population, 43 percent of women and 31 percent of men between the ages of 18 and 59 repeatedly experience it. Sexual dysfunction includes lacking interest in sex, problems with arousal, not enjoying sex, and anxiety about sexual performance. Indeed, feeling good in general has significant impact on sexual function, with those people unhappy or depressed more likely to experience difficulties. Arousal problems affect over 20 million American males, about two in 10 adult men, with such difficulties often associated with or accompanied by some sort of depression. Meanwhile, prescription antidepressants actually exacerbate the situation, since a frequent side effect of their use is sexual dysfunction. In fact, sexual response diminishes in up to 75% of prescription antidepressant users.

There is a need for treatments to reduce depression or otherwise better mood with an accompanying enhancement of sexual response or desire, or at least no sexual dysfunction.

Prior work on the compounds of the invention has solely been on 6-methoxy-2,3-benzoxazolinone (6-MBOA). Its role in strengthening the resistance of monocotyledonous plants against a wide range of insect pests has been much studied. 6-MBOA and its chemical precursors also have allelopathic properties that inhibit root and shoot growth in competing species. Furthermore, it has antimicrobial properties. 6-MBOA appears constitutively during early stages of growth, localized in those tissues most exposed to microbial and insect attack.

It had been long suspected that compounds in plants affect the seasonal reproductive output of wild rodents. In 1981, 6-MBOA became the first naturally occurring compound in a plant verified as impacting seasonal reproductive cycling. Since then, a substantial body of work has accumulated on 6-MBOA as an initiator of seasonal breeding and an effector of population size for many rodents and a few birds. Compounds related to and possibly co-occurring with 6-MBOA remain unexplored in this regard.

6-MBOA is passed from adult females to offspring during gestation and lactation, with increased growth and greater gonadal size in the recipient young. Juveniles rely on the interaction of maternal photoperiod history and 6-MBOA to time the onset of growth and puberty. Adults fed a diet containing 6-MBOA produce more female progeny. When 6-MBOA is fed to pregnant females, gonadal development in the male offspring is enhanced.

For rodents, the inhibitory effects of melatonin on growth and reproduction are blocked partially by 6-MBOA (Gower et al., "Reproductive responses of male *Microtus montanus* to photoperiod, melatonin, and 6-MBOA", *Journal of Pineal Research*, 8:297–312, 1990). 6-MBOA may obstruct melatonin at the melatonin receptors or act independently to check melatonin action (Sweat et al., "Uterotropic 6-methoxybenzoxazolinone is an adrenergic agonist and melatonin analog, *Molecular and Cellular Endocrinology*, 57:131–138, 1988). The high melatonin levels that accumulate in the presence of 6-MBOA may cause desensitization of melatonin receptors (Daya et al., "Effect of 6-methoxy-2-benzoxazolinone on the activities of rat pineal N-acetyltransferase and hydroxyindole-O-methyltransferase and on melatonin production", *Journal of Pineal Research*, 8:57–66, 1990), but not in all rodents (Anderson et al., "Effects of melatonin and 6-methoxybenzoxazolinone on photoperiodic control of testis size in adult male golden hamsters", *Journal of Pineal Research*, 5:351–65, 1988). This compound stimulates rather than inhibits melatonin biosynthesis and does not prevent stimulation of melatonin synthesis by norepinephrine (Yuwiler et al., "Effects of 6-methoxy-2-benzoxazolinone on the pineal melatonin generating system. *J. Pharmacol. Exp. Ther.* 233:45–50, 1985). 6-MBOA acts at both the a- and b-adrenergic receptors (Daya et al., "Effect of 6-methoxy-2-benzoxazolinone on the activities of rat pineal N-acetyltransferase and hydroxyindole-O-methyltransferase and on melatonin production", *Journal of Pineal Research*, 8:57–66, 1990), and stimulates adenylcyclase activity in the pineal, hypothalamus and pituitary glands (Sweat et al., "Uterotropic 6-methoxybenzoxazolinone is an adrenergic agonist and melatonin analog, *Molecular and Cellular Endocrinology*, 57:131–138, 1988). Certain responses to 6-MBOA, like uterine hypertrophy, can be duplicated with estrogen, but 6-MBOA is not an estrogenic compound (Gower, "Endocrine effects of the naturally occurring reproductive stimulant, 6-methoxybenzoxazolinone", Ph.D. Thesis, University of Utah, Salt Lake City, Utah, 116p., 1990). Also, 6-MBOA increases the rate of synthesis of follicle stimulating hormone (Butterstein et al., "The plant metabolite 6-methoxybenzoxazolinone interacts with follicle-stimulating hormone to enhance ovarian growth", *Biology of Reproduction*, 39:465–71, 1988) and pituitary prolactin (Vaughan et al., "Hormonal consequences of subcutaneous 6-methoxy-2-benzoxazolinone pellets or injections in prepubertal male and female rats", *Journal of Reproduction and Fertility*, 83:859–66, 1988). Hypothalamic luteinizing hormone-releasing hormone contents and pituitary gland weights are greater for at least one rodent species implanted with capsules containing 6-MBOA (Urbanski et al., "Influence of photoperiod and 6-methoxybenzoxazolinone on the reproductive axis of inbred LSH/Ss Lak male hamsters. *Journal of Reproduction and Fertility,* 90:157–163, 1990). The above studies cumulatively point to 6-MBOA acting in the pineal-hypothalami-pituitary axis, possibly as a melatonin agonist and at the a- and b-adrenergic receptors in its own right.

The inventors recognized that 6-MBOA and the indoleamine, melatonin, share a structural similarity. However, melatonin exacerbates symptoms of dysphoria in depressed people. 6-MBOA, as a melatonin agonist, could prove contrary in this regard and actually improve mood. Yet, the inventors are not aware of any prior art that has explored or suggested the use of 6-MBOA and related compounds as having psychotropic effects in humans, particularly with respect to depression or mood.

An object of the invention is to develop therapies for depression and sexual dysfunction entailing use of compounds belonging to related chemical families, of which 6-MBOA is a member. Pursuant to this end, a further object is to develop methods for getting said compounds from plant and animal sources in amounts suitable for human therapeutic use.

SUMMARY OF THE INVENTION

According to the invention, it has been found that certain phenolic compounds, related to each other by shared structural similarities and having structural similarities with melatonin, are effective in bettering mood, improving sexual desire and performance, and as an adjunctive therapy for weight loss and substance abuse and addiction. The compounds of the invention naturally exist as plant secondary metabolites in the early growth of monocotyledonous plants, become concentrated from their ingestion within certain animal parts, or can be synthesized by chemical means. The invention includes therapies using the compounds of the invention for treating depression and sexual dysfunction, as well as adjunctive therapies for achieving weight loss and problems of substance abuse and addiction. The therapeutic method comprises the ingestion of the compounds of the invention over a certain period of time, or other means for getting the compounds of the invention into the body. Both males and females benefit from ingesting the compounds of the invention, while still contained in dried leaves from plants with such compounds or taken as purified and/or synthesized preparations. It appears that the compounds of the invention act as antidepressants without the undesirable side effects of currently used antidepressants.

The compounds include a phenol molecule to which are covalently linked an oxygen-containing group, a nitrogen- or another oxygen-containing group, and a $C_1$–$C_4$ alkoxy group.

A source of the compounds of the invention is in monocotyledonous plants in their early growth stages. To obtain these compounds at concentrations suitable for human therapeutic use from such monocotyledonous plants, harvest of these plants at an early life history stage and drying using explicit parameters, as well as specific analytical criteria to ascertain suitability, are employed. However, it is also possible to get the compounds of the invention at concentrations suitable for human therapeutic use from animals parts, including, but not necessarily limited to, the velvet antler tips of deer and elk (Cervidae), where they become concentrated after ingestion by the animal of sprouting and otherwise immature grasses. The compounds of the invention can also be obtained through chemical synthesis.

BRIEF DESCRIPTION OF THE DRAWINGS

The invention will be described in more detail below, with reference being made to the accompanying drawings, in which:

FIG. 4 summarizes the effects of consuming compounds of the invention by human males on depression or mood and sexual response;

DETAILED DESCRIPTION OF THE PREFERRED EMBODIMENT

Figure 1:
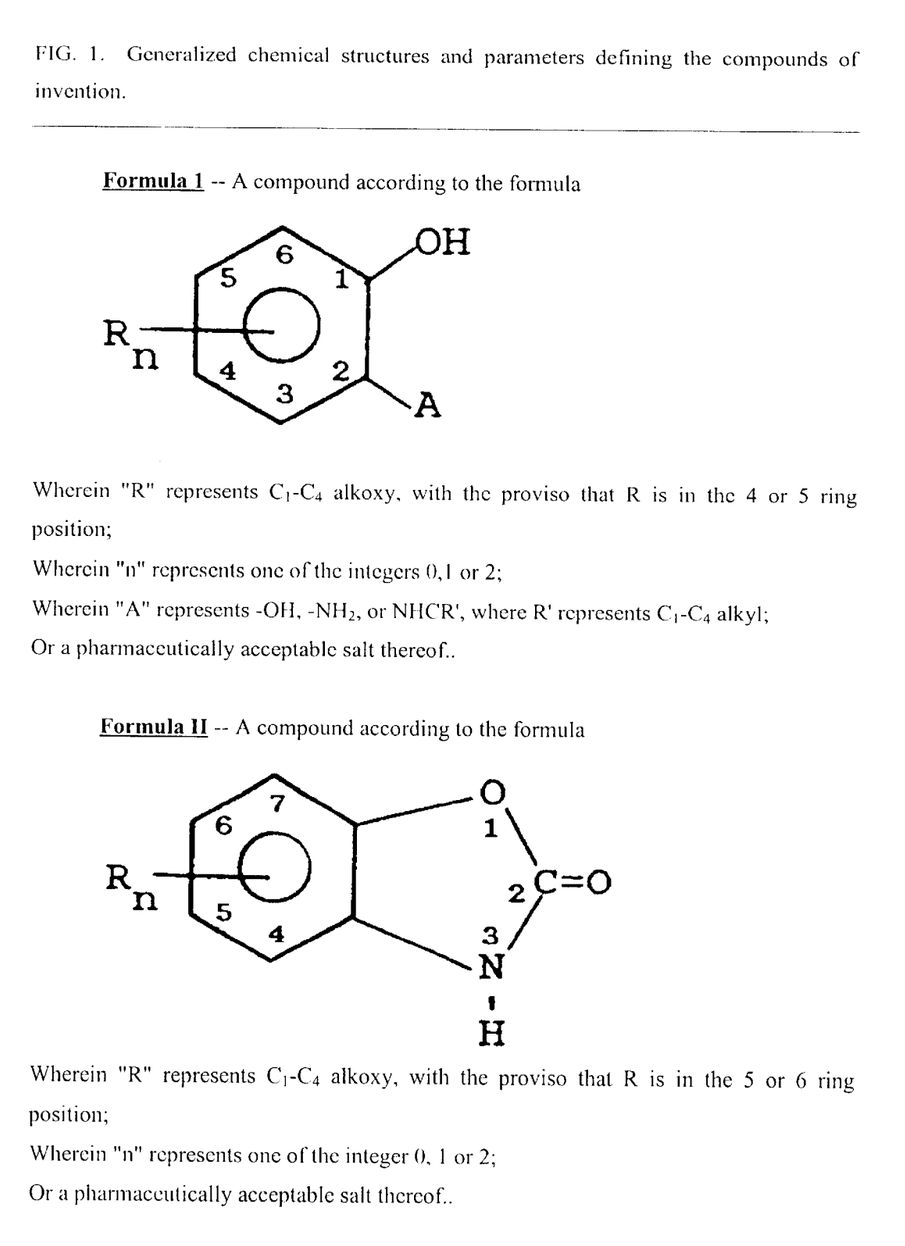
FIG. 1 shows the general chemical structures and parameters defining the compounds of the invention.

The compounds of the invention have in common a phenol molecule to which are covalently linked an oxygen-containing group, a nitrogen- or another oxygen-containing group, and a $C_1$–$C_4$ alkoxy group. Using standard conventions for depicting chemical structures, FIG. 1 discloses the chemical structures and specific parameters defining the compounds of the invention. The chemical structures and specific parameters delimiting the compounds of the invention are also defined below as follows:

Formula I—A chemical composition according to the formula

Wherein "R" represents $C_1$–$C_4$ alkoxy, with the proviso that R is in the 4 or 5 ring position;

Wherein "n" represents one of the integers 0, 1 or 2;

Wherein "A" represents —OH, —$NH_2$, or NHCR', where R' represents $C_1$–$C_4$ alkyl;

or a pharmaceutically acceptable salt thereof.

Formula II—A chemical composition according to the formula

Wherein "R" represents $C_{1-C4}$ alkoxy, with the proviso that R is in the 5 or 6 ring position;

Wherein "n" represents one of the integers 0, 1 or 2;

or a pharmaceutically acceptable salt thereof.

Formula III—A chemical composition according to the formula

Wherein "R" represents $C_1$–$C_4$ alkoxy, with the proviso that R is in the 6 or 7 ring position;

Wherein "n" represents one of the integers 0, 1 or 2; or a pharmaceutically acceptable salt thereof.

It has been found that compounds of the invention, when ingested or otherwise introduced into the user's body, are effective as an antidepressant in that it betters mood and reduces or relieves symptoms of depression, improves sexual desire and performance, and can be used effectively adjunctively in weight loss therapy and in therapy for substance abuse and addiction. The compounds may be ingested in the form of ground plant parts in which they naturally occur, such as the ground leaves of immature corn plants, as an extract from animal parts, such as the velvet antler tips from deer or elk, or as a chemically synthesized compound in a pharmaceutically acceptable carrier.

The compounds of the invention may be administered orally in the form of tablets, capsules, suspensions, solutions or other means suitable for such ingestion, perhaps as an admixture with other compounds to enhance absorption into the blood stream or to otherwise assist in achieving the desired effects.

The compounds of the invention may also be administered parenterally, as a subcutaneous, intramuscular or intravenous injection, or by way of an implant for sustained release. When administered parenterally, the compounds of the invention are to be dissolved in physiologically acceptable liquid media and/or otherwise compounded in accordance with the known pharmaceutical art. Another mode of administering the compounds of the invention may be a transdermal patch, in which entry of the compounds of the invention into the body is facilitated via acceptable carrier molecules.

Unless otherwise defined, the technical and scientific terminology used herein has the same meaning as understood by those informed of the art to which this invention belongs.

EXAMPLES

Described herein are preferred or representative materials and methods for the practice of the invention. The materials and methods, along with the examples, are only illustrative in the sense that these are not intended to be limiting.

Example 1

The Similar Physiological Effects of the Compounds of the Invention

Figure 2:
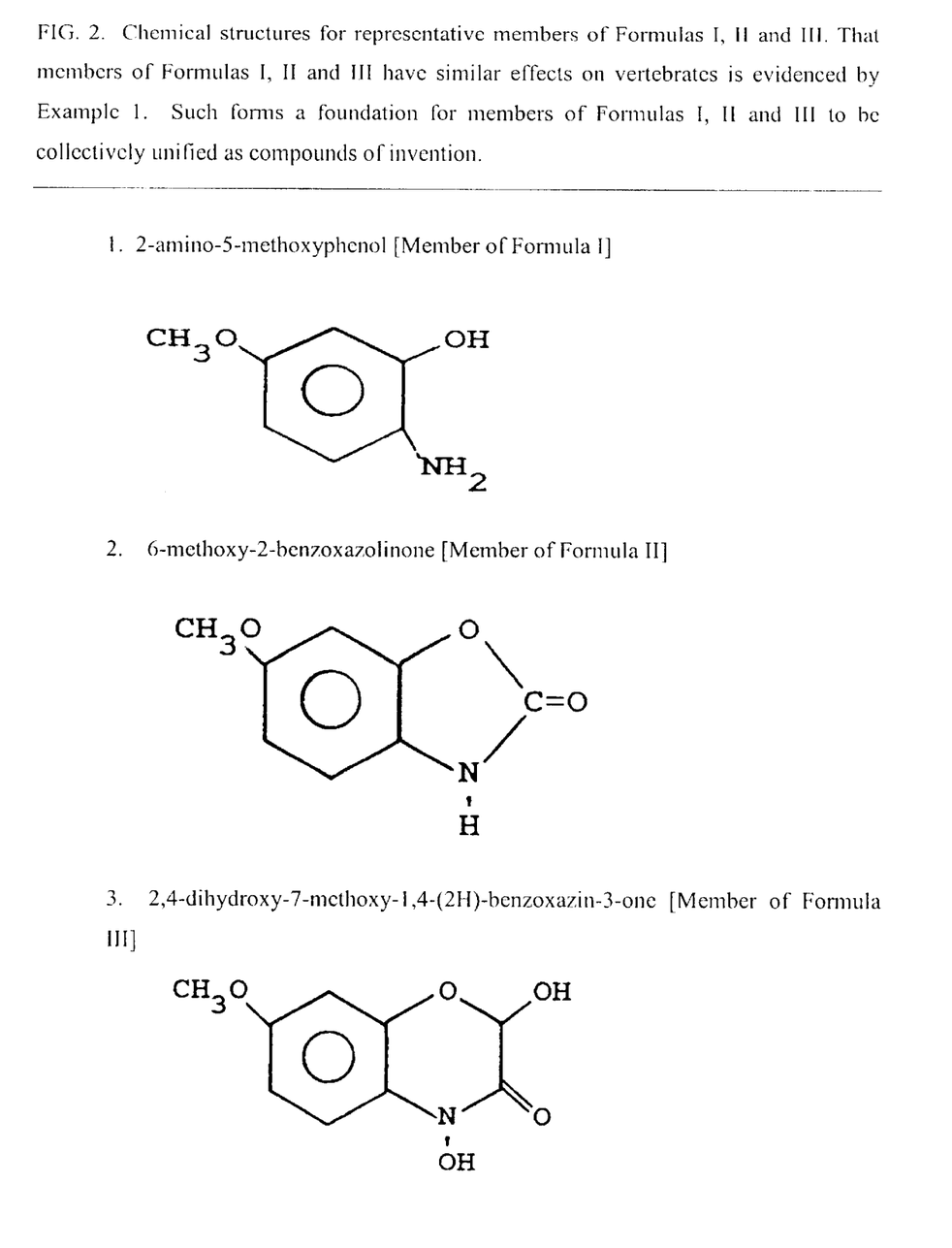
FIG. 2 shows the chemical structures for representative compounds of the invention.

Representative compounds of Formulas I, II, and III are shown in FIG. 2. That compounds of Formulas I, II and III have like physiological properties, and as such can be considered as similar or equivalent for therapeutic purposes, was tested via a rodent model. Female montane voles, *Microtis montanus*, received intraperitoneal injections of representative compounds belonging to Formulas I, II and III, and shown in FIG. 2, for three consecutive days and sacrificed 24 hours after the last injection to examine uterine weight response. To assess the properties of each representative compound, pure ones made by chemical means (University of Utah Department of Chemistry, Salt Lake City, Utah) were prepared specifically for this test. All compounds were injected at a dose level of 5 µg/day, dissolved in 5% propylene glycol for a total injection volume of 0.5 ml. Control animals received 0.5 ml of 5% propylene glycol only. All voles were 4–5 weeks old and weighed 25–29 g.

Figure 3:
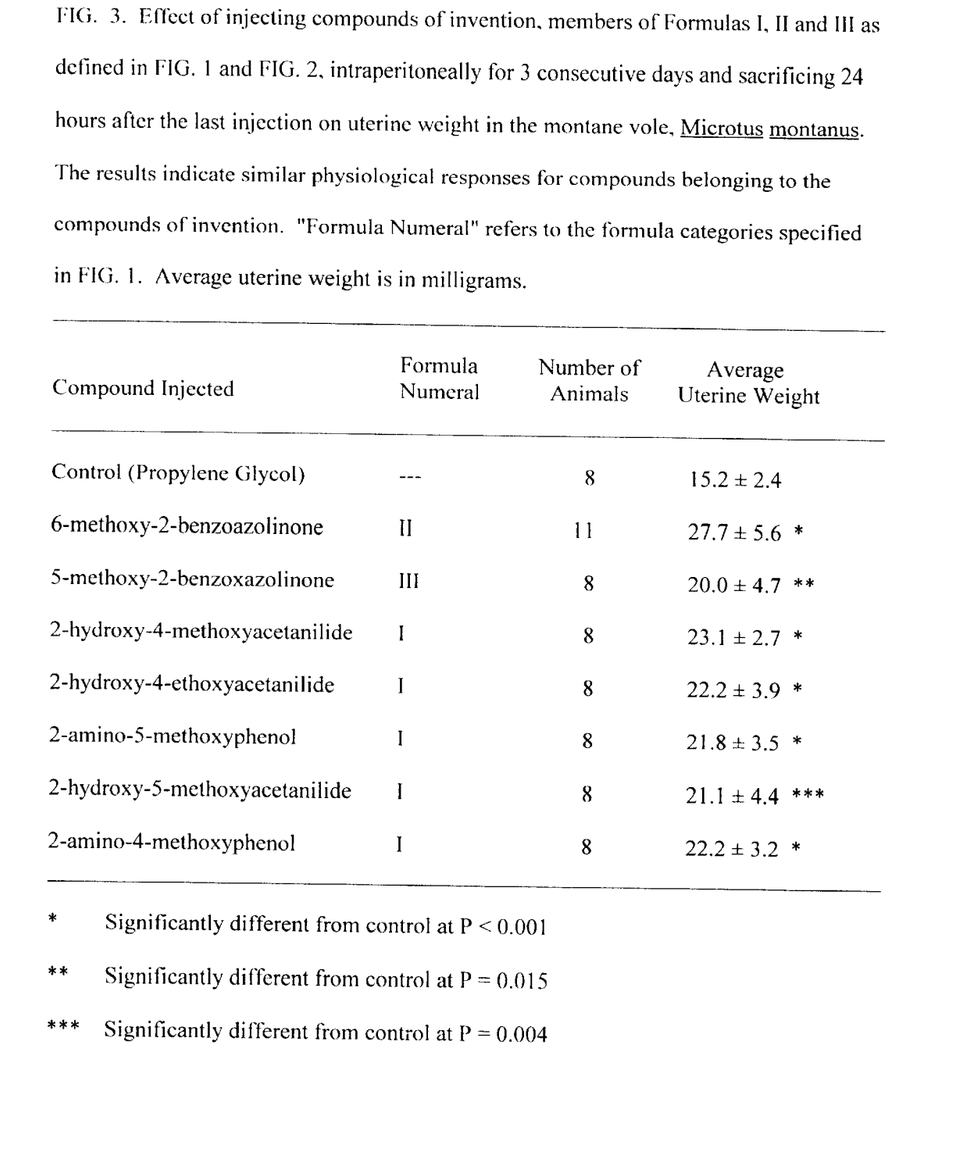
FIG. 3 shows the effects of injecting representative compounds of the invention on uterine weight in a rodent.

All compounds belonging to Formulas I, II and III caused a statistically significant increase in uterine weights (FIG. 3). On average, the uterine weight in voles receiving these was 22.8 g, 50% greater than for the control group. The greatest average weight increase, 82% more than the uterine weight for the control voles, was in those females administered 6-methoxy-2-benzoxazolinone, but even the least effect of a compound belonging to Formulas I, II or III, that for 5-methoxy-2-benzoxazolinone, entailed a 32% increase in uterine weight. The results show that physiological effects or modes of action are held in common by the compounds of the invention.

Example 2

Compounds of the Invention as an Antidepressant and Aphrodisiac in Human Males

This component of the invention relates to a method for lessening depression and otherwise bettering mood or feelings of well-being, said method comprising the administration to human males of an effective amount of one or more of the compounds of the invention, defined above and in FIG. 1. This component of the invention also relates to a method for treating sexual dysfunction or otherwise increasing sexual desire and performance, including but not necessarily limited to lacking interest in sex, problems with arousal, not enjoying sex, and anxiety about sexual performance, said method comprising the administration of an effective amount of one or more of the active compounds of the invention.

A double-blind crossover study was done on human males to test compounds of the invention as a therapeutic agent for treating depression or otherwise elevating mood as well as bettering sexual function. The trial had three phases, each two weeks in duration, during which participants took compounds of the invention for one phase or two weeks. The daily dose was made up from compounds of the invention naturally contained in the ground leaves from immature corn plants, 30–45 cm tall, standardized with synthesized 6-methoxy-2-benzoxazolinone, to a total of 15-mg 6-methoxy-2-benzoxazolinone. A dose of 15-mg was selected because this was considered a likely minimum effective daily amount for humans, extrapolated from prior studies on rodents, rabbits and other animals. Previous anecdotal trials on humans done by the inventors suggested that a 15-mg daily dose had a desirable effect, but no adverse consequences to health.

Weekly assessments of depression or mental well being and sexual function were done via widely accepted indices: to quantify depression and generalized anxiety disorders, the Hospital Anxiety and Depression Scale (HAD); and for sexual desire, psychological arousal, and overall sexual outlook, the Arizona Sexual Experience Index (ASEX).

Phase One lasted 14 days, during which participants took daily doses of the invention or a placebo. Assignation of the invention or placebo to male participants was done randomly. Immediately prior to the 14 days comprising Phase One, an initial physical examination and blood analysis were done. At that time, each male filled out HAD and ASEX forms to assess mental well being and sexual function, was checked for sitting and standing blood pressure and pulse, and gave the blood sample needed for the biochemical analyses.

Phase Two consisted of a seven-day period immediately after Phase One, during which neither invention nor placebo was taken. During Phase Two, physical examination and laboratory analyses were again done. In Phase Three which lasted 14 days, participants again took either invention or a placebo. Assignation of the invention or placebo was done according to the sort of capsule taken during Phase One. If a participant took a compound of the invention in Phase One, then placebo was administered during Phase Three, and vice versa. Immediately after finishing Phase Three, a physical examination and laboratory analyses were again done. After completing Phase Three, each participant was asked prepared questions as well as solicited for any comments and impressions concerning invention use.

The results are tabulated in FIG. 4, and these indicate that the compounds of the invention have significant positive effect on depression or mood. Fourteen of the 15 participants properly completed the study and only data for these individuals were used for analysis. HAD scores exceeding 20.0 denote clinical depression, but lower ones can also be associated with dispirited mood. Only two males entered the trial with HAD values exceeding the clinical minimum (21.0 and 23.0). Still, 12 of 14 subjects showed bettered mood, improved feelings of well being or lessened depression after taking compounds of the invention. Decreases in HAD scores over the two-week timespan were as much as 15 and averaged 5.2. The two clinically depressed subjects showed decreases in HAD values of 5.0 and 15.0. The average HAD score went from 13.5 at the onset of the study to 9.1 after two weeks of taking compounds of the invention, very significant statistically. Participants showed no statistically detectable changes while taking placebo.

After taking compounds of the invention for two weeks, 5 of 14 participants had lessened ASEX values, indicating improved sexual response or lessened sexual anxiety, while only 2 of 14 males showed the same after two weeks on placebo. Statistical significance was not found for the ASEX changes, but such could be attributed to a small sample size. Sexual benefits of the compounds of the invention were also obviated in the trial through the exit interviews given to all participants. While taking these, a majority of males reported morning erections of the penis greater in size, duration or frequency than usually experienced when not taking the compound. Also, comments by the majority centered about feeling "like a teenager (direct quote)" in terms of energy, sexual and otherwise. It should be noted that personal situations were complicated by unwilling or lacking sex partners. Twelve of 15 participants also expressed an unsolicited desire to continue using the compounds of the invention. They stated a belief that the compounds of the invention could prove useful to them in a sexual context.

Example 3

Compounds of the Invention As an Antidepressant in Human Females

This example further relates to a method for lessening depression and otherwise bettering mood or feelings of well-being, said method comprising the administration to human females of an effective amount of the compounds of the invention, defined above and in FIG. 1. Compounds of the invention were used to treat eight females with clinical depression, which for three females had been ongoing for at least one year. Participants took the same dose of compounds of the invention as in Example 2, 15-mg each day. A HAD was administered to participants prior to beginning daily doses. Each participant was interviewed every two weeks to check for adverse side effects and for comments on use of the compounds of the invention. A HAD Index was again administered upon completion of the six-week trial.

Figure 5:
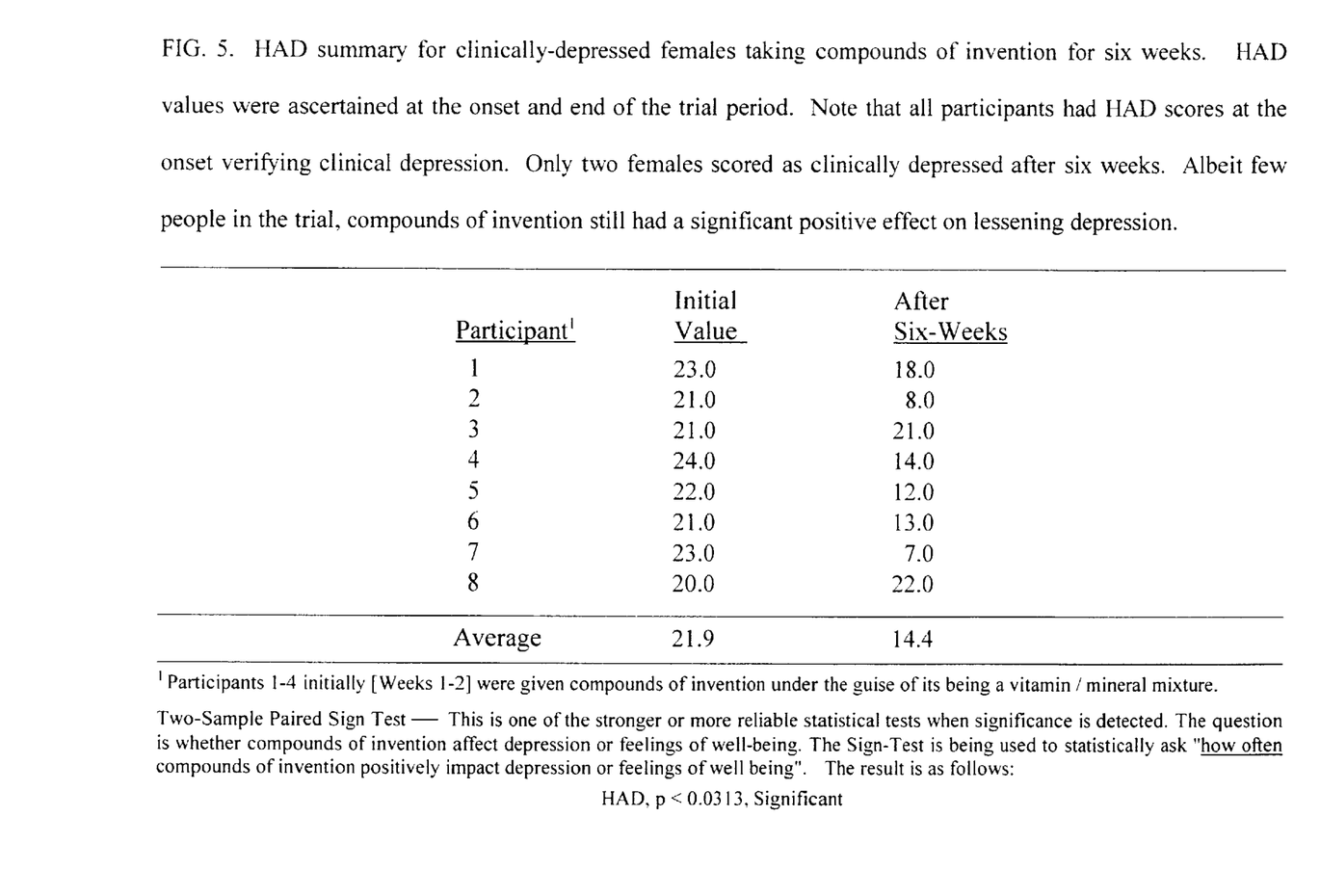
FIG. 5 summarizes the effects of consuming compounds of the invention by human females on depression or mood.

Results of the study are tabulated in FIG. 5. These indicate that the compounds of the invention significantly lessen depression. Initial HAD scores exceeded 20 for all subjects. All females were clinically depressed, and their HAD scores averaged 21.9 [FIG. 4]. Six of eight participants showed responses to compounds of the invention in which HAD values decreased 5–16 points, an average decrease of 10.5 over the six-week timespan. The overall average HAD score decreased from 21.9 (clinically depressed) at trial onset to 14.4 (not clinically depressed) after six weeks of use, with two participants ending with HAD values of 8 and 7. There were only eight females in the trial, but decreases in HAD scores were still statistically significant [$p<0.031$]. The antidepressant properties of the compounds of the invention are obviated.

Both excess weight and substance abuse are characterized by either primary or secondary depression. Since such psychological factors affecting excess weight and substance abuse must be treated along with the physiological ones for therapies to be effective in the long term, the compounds of the invention comprise adjunctive treatments for achieving weight loss or reducing the risk of relapse in persons with substance abuse or addiction problems.

Example 4

Compounds of the Invention at Concentrations Suitable for Human Therapies from Plants Harvested and Processed in Unique Fashion Example 4 relates to a method for obtaining compounds of the invention at concentrations suitable for human therapies from plants grown to an immature stage of growth. "Concentrations suitable for human therapies" means that compounds of the invention in 10 grams or less of dried plant material make up a daily dose (e.e., 15 mg compounds of the invention as 6-methoxy-2-benzoxazolinone). Specific harvesting and drying conditions are specified herein, as are analytical parameters for determining crop quality. By "specific harvesting and drying conditions", it is meant that compounds of the invention are obtained from plants via circumstances differing from the usual manner in which the plants are handled for the terminal product.

As an example, corn, Zea mays, is typically grown to its adult or matured states for its seed-laden cob. At the immature growth stage at which compounds of the invention occur, corn plants have a biomass that portends harvest of a substantial amount of leaf material containing the compounds of the invention at concentrations suitable for human therapies. Hence, dried corn leaves from immature plants become appropriate for the human therapies elucidated herein, or the dried leaves are a resource for the concentration, extraction and purification of the compounds of the invention. There are other monocotyledonous plants with the natural production of compounds of the invention at concentrations suitable for human therapies. These are not precluded from invention by the example of corn. In all cases, harvest and processing needs to be done in a novel and unique fashion relative to the usual manner in which the plants are handled, and the analytical parameters for indirectly determining crop quality with respect to the compounds of the invention, described below, are applicable.

Growing corn to obtain the compounds of the invention is initially done in a conventional fashion, but seeds are planted more densely than is the case for conventional crops because of the smaller size of plants at harvest. Harvest time is done while plants are immature. For corn, this happens when plants are no more than 30–45 centimeters tall, about five weeks after planting, contrasting with the more than 180 centimeters and 4–5 months of growing time typical for mature corn. For corn, harvesting is done by cutting plants at 3–4 centimeters above the ground. Severed plants are then gathered and dried at temperatures held at 40–45° C. Empirical studies showed that this temperature range helps maximize conversion of the precursors of compounds of the invention to the active molecules.

In a trial plot in southern Illinois, approximately 38,000 corn plants yielded 137 kilograms (300 pounds) of dried (96% dry weight) corn leaves with suitable levels of compounds of the invention. Analyses via mass spectroscopy showed that substantive amounts of the compounds of the invention were in dried corn leaves after 5 weeks of growing time. Five random samples of dried corn leaves were obtained for analysis. For each dried corn leaf sample, a one-gram portion was homogenized in 10-ml distilled water, incubated at 25° C. for 1 hour, boiled for 30 min, and then centrifuged for 10 min at 3600 rpm. The resulting supernatant was extracted 3 times with 10 ml reagent-grade dichloromethane per extraction. The three extracts were combined and allowed to air dry, after which the dried residue was stored in a tightly stoppered glass tube.

The dried residue was analyzed for 6-MBOA by gas-chromatographic mass spectroscopy. A Dupont Model DP102 device with an integrator and a SP2250 GC column isothermal at 200° C. (Dupont, Wilmington, Del.) was used. A standard curve for 6-MBOA was obtained using 0.06-, 0.60- and 1.20-$\mu$g injections of pure, synthetic 6-MBOA (Sigma, Saint Louis, Mo.) in methanol solution and was reproducible at a 5% level.

6-MBOA occurred in dried corn leaves at levels suitable for human consumption. Samples averaged 10 mg/g 6-MBOA, with individual samples assaying as follows: 8, 9, 10, 10, and 12 mg/g 6-MBOA. At such concentrations, less than two grams dried corn leaves are needed to make up a daily human dose. This makes corn leaves, as uniquely grown, harvested and dried herein, a suitable source of compounds of the invention. For comparisonal purposes, leaves from plants grown more than 8 weeks were analyzed for 6-MBOA. Virtually none was present.

Previous work by the inventors indicated that higher levels of the compounds of the invention are associated with multiple biochemical parameters that indicate crop quality or adequacy with respect to the compounds of the invention. In those plants containing compounds of the invention at concentrations suitable for human use total phenols are at concentrations greater than 17.0 mg/gm (dry weight) but combined amounts of 4-hydroxycinnamic acid and 4-hydroxy-3-methoxycinnamic acid total no more than 1.5 mg/gm (dry weight), as determined through chromatography. For invention, the above mentioned parameters for total phenols and combined amounts of 4-hydroxycinnamic acid and 4-hydroxy-3-methoxycinnamic acid are instituted here as elements of the invention as it pertains to plants. For the corn leaf samples of FIG. 4, total phenols averaged 19.1 mg/gm and the cumulative total for cinnamic acids averaged 0.9 mg/gm.

Example 5

Compounds of the Invention from Parts of Animals

The main food of deer and elk (Cervidae) for most of the year is browse, the growing tips of low-growing, woody plants. However, casting of hard antlers from the previous year coincides with a spring flush in natural pasturage and an accompanying shift to a diet of grasses, chiefly sprouting and immature ones. Such grasses are at developmental stages in which 6-MBOA and related compounds are most prevalent.

After casting, new antlers begin their development. These growing antlers are nourished by blood vessels from a covering of skin, called velvet. An antler grows from the tip with tissue laid down as the tip advances. A velvet antler tip has a soft cartilaginous internal structure and high fat content, contrasting the rest of the antler with its ossified cartilage and little fat.

Air-dried and freeze-dried velvet antler samples were obtained. These came from commercially farmed Canadian Wapiti and New Zealand red deer, both subspecies of elk, *Cervus elaphus*. All animals had been maintained on grassy pasturage. The samples were from velvet antlers that had been growing 55 to 65 days, and included both tips, defined as the region 5 cm or less in length starting at the apex, as well as other, more matured parts of the antler.

For each sample of dried antler, a one-gram portion was homogenized in 10-ml distilled water, incubated at 25° C. for 1 hour, boiled for 30 min, and then centrifuged for 10 min at 3600 rpm. The resulting supernatant was extracted 3 times with 10 ml reagent-grade dichloromethane per extraction. The three extracts were combined and allowed to air dry, after which the dried residue was stored in a tightly stoppered glass tube.

The dried residue was analyzed for 6-MBOA by gas-chromatographic mass spectroscopy. A Dupont Model DP102 device with an integrator and a SP2250 GC column isothermal at 200° C. (Dupont, Wilmington, Del.) was used. A standard curve for 6-MBOA was obtained using 0.06-, 0.60- and 1.20-$\mu$g injections of pure, synthetic 6-MBOA (Sigma, Saint Louis, Mo.) in methanol solution and was reproducible at a 5% level.

Figure 6:
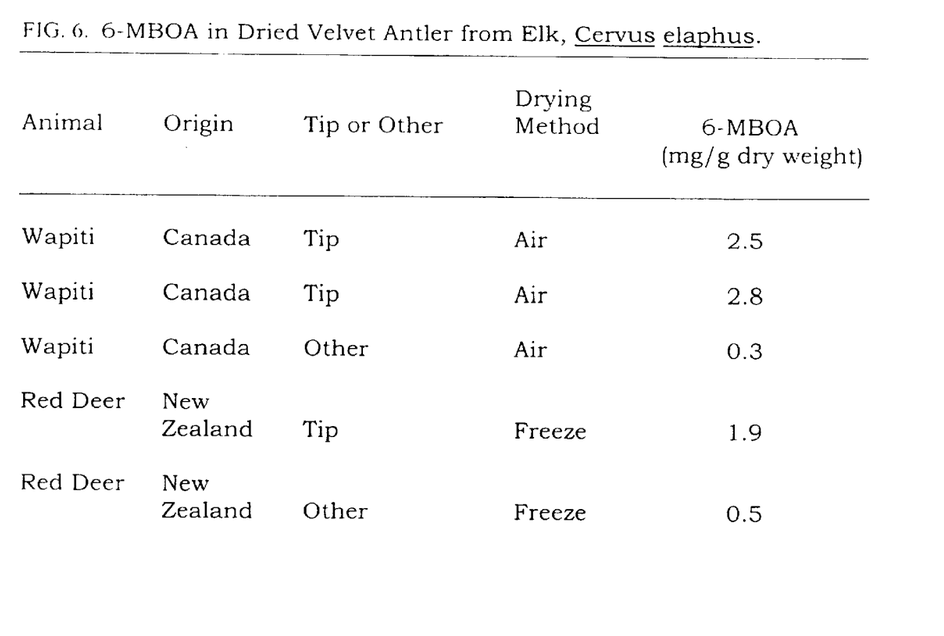
FIG. 6 shows the 6-methoxy-2-benzoxazolinone contents of air-dried and freeze-dried velvet antler samples from elk, *Cervus elaphus.*

Results are shown in FIG. 6. 6-MBOA was present in all tip samples, with little or none present in those from the more matured parts of the antler. Notably, amounts of 6-MBOA from velvet antler tips exceeded those typically found in grasses less than a week after sprouting, the stage of growth with the most 6-MBOA (Epstein et al., "Dynamics of 6-methoxybenzoxazolinone in winter wheat: effects of photoperiod and temperature", Journal of Chemical Ecology, 12:2011–2021, 1986). These results show that ingested 6-MBOA is accumulated or concentrated in velvet antler tips, and as such represent a means for obtaining the compounds of the invention in concentrations suitable for human use.

Many animals eat grasses and other monocotyledous plants. Such animals may also be accumulating compounds of the invention in body parts, most likely in those characterized by high fat contents. Obtaining compounds of the invention from body parts other than the antlers of elk and deer and from animals other than elk or deer are not precluded from invention.

While specific dose levels are used in the Examples, these are merely examples and effective dose levels may vary to a large extent, and preferred dose levels may vary with the conditions being treated and the size or sex of the person being treated. Dose levels do not appear to be critical as long as an effective amount is given.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. A process for treating sexual desire, arousal and performance in humans by the administration of a therapeutically effective amount of one or more chemical compositions defined as:

Wherein "R" represents $C_1$–$C_4$ alkoxy, with the provision the R is in the 4 or 5 ring position;
Wherein "n" represents one of the integers 0, 1 or 2;
Wherein "B" represents H and "A" represents —OH, —$NH_2$ or NHCR', where R' denotes $C_1$–$C_4$ alkyl; and "B A" represents or or pharmaceutically acceptable salts thereof.

2. A process according to claim 1, wherein at least one of the chemical compositions is defined as:

Wherein "R" represents $C_1$–$C_4$ alkoxy, with stipulation that R is in the 4 or 5 ring position;
Wherein "n" represents one of the integers 0, 1 or 2; or pharmaceutically acceptable salts thereof.

3. A process according to claim 1, wherein at least one of the chemical compositions is obtained from one or more monocotyledonous plants selected from the group consisting of corn, wheat, barley, rye, oats, rice, sorghum, millet, bamboo, barley-like grasses, and wild grasses, by growing the plant to an immature life history stage, harvesting the plant, and drying the harvested plant.

4. A process according to claim 3, wherein the harvested plant is dried at a temperature in the range of 40° C. to 45° C.

5. A process according to claim 3, wherein the dried harvested plant contains combined amounts of 4-hydroxycinnamic acid and 4-hydroxy-3-methoxycinnamic acid totaling no more than 1.5 mg/gm (dry weight).

6. A process according to claim 3, wherein the harvested plant is immature corn.

7. A process according to claim 6, wherein the immature corn has been grown to a height that does not exceed 30–45 centimeters.

8. A process according to claim 6, wherein the immature corn has been grown for no more than five weeks after planting.

9. A process according to claim 1, wherein the administered chemical composition comprises a daily dosage of 15 mg.

10. A process according to claim 1, wherein the dried harvested plant contains phenols in total amounts greater than 17.0 mg/gm (dry weight).

11. A process according to claim 10, wherein the dried harvested plant contains combined amounts of 4-hydroxycinnamic acid and 4-hydroxy-3-methoxycinnamic acid totaling no more than 1.5 mg/gm (dry weight).

12. A process according to claim 10, wherein the harvested plant is immature corn, *Zea Mays*.

13. A process according to claim 12, wherein the immature corn has been grown to a height that does not exceed 30–45 centimeters.

14. A process according to claim 10, wherein the immature corn has been grown for no more than five weeks after planting.

15. A process according to claim 1, wherein said chemical composition is administered in a manner selected from the group consisting of: (1) orally, in the form of tablets, capsules, suspensions, solutions and other means suitable for ingestion; (2) parenteral injection, in the form of subcutaneous, intramuscular, intravenous; (3) implant for sustained release; and (4) transdermal patch.

16. A process for treating depression in humans by the administration of a therapeutically effective amount of one or more chemical compositions defined as:

Wherein "R" represents $C_1$–$C_4$ alkoxy, with the provision the R is in the 4 or 5 ring position;
Wherein "n" represents one of the integers 0, 1 or 2;
Wherein "B" represents H and "A" represents —OH, —$NH_2$ or NHCR', where R' denotes $C_1$–$C_4$ alkyl; and "B A" represents or -continued or pharmaceutically acceptable salts thereof.

17. A process according to claim 16, wherein the administered chemical composition comprises a daily dosage of 15 mg.

18. A process according to claim 15, wherein at least one of the chemical compositions is obtained from one or more monocotyledonous plants selected from the group consisting of corn, wheat, barley, rye, oats, rice, sorghum, millet, bamboo, barley-like grasses, and wild grasses, by growing the plant to an immature life history stage, harvesting the plant, and drying the harvested plant.

19. A process according to claim 18, wherein the harvested plant is dried at a temperature in the rage of 40° C. to 45° C.

20. A process according to claim 18, wherein the dried harvested plant contains phenols in total amounts greater than 17.0 mg/gm (dry weight).

21. A process according to claim 18, wherein the dried harvested plant contains combined amounts of 4-hydroxycinnamic acid and 4-hydroxy-3-methoxycinnamic acid totaling no more than 1.5 mg/gm (dry weight).

22. A process according to claim 18, wherein the harvested plant is immature corn.

23. A process according to claim 22, wherein the dried immature corn contains phenols in total amounts greater than 17.0 mg/gm (dry weight).

24. A process according to claim 22, wherein the dried immature corn contains combined amounts of 4-hydroxycinnamic acid and 4-hydroxy-3-methoxycinnamic acid totaling no more than 1.5 mg/gm (dry weight).

25. A process according to claim 22, wherein the immature corn is *Zea Mays*.

26. A process according to claim 22, wherein the immature corn has been grown to a height that does not exceed 30–45 centimeters.

27. A process according to claim 22, wherein the immature corn has been grown for no more than five weeks after planting.

28. A process according to claim 18, wherein the harvested plant has been grown to a height that does not exceed 30–45 centimeters.

29. A process according to claim 18, wherein the harvested plant has been grown for no more than five weeks after planting.

30. A process according to claim 16, wherein said chemical composition is administered in a manner selected from the group consisting of: (1) orally, in the form of tablets, capsules, suspensions, solutions and other means suitable for ingestion; (2) parenteral injection, in the form of subcutaneous, intramuscular, intravenous; (3) implant for sustained release; and (4) transdermal patch.

31. A process for treating sexual desire, arousal and performance in humans by the administration of a therapeutically effective amount of one or more chemical compositions defined as:

Wherein "R" represents $C_1$–$C_4$ alkoxy, with stipulation that R is in the 4 or 5 ring position;

Wherein "n" represents one of the integers 0, 1 or 2; or pharmaceutically acceptable salts thereof.

32. A process according to claim 31, wherein one of said chemical compositions comprise 6-methoxy-2,3-benzoxazolinone defined as:

or pharmaceutically acceptable salts thereof.

33. A process according to claim 31, wherein the administered chemical composition comprises a daily dosage of 15 mg.

34. A process according to claim 31, wherein at least one of the chemical compositions is obtained from one or more monocotyledonous plants selected from the group consisting of corn, wheat, barley, rye, oats, rice, sorghum, millet, bamboo, barley-like grasses, and wild grasses, by growing the plant to an immature life history stage, harvesting the plant, and drying the harvested plant.

35. A process according to claim 34, wherein the dried harvested plant contains phenols in total amounts greater than 17.0 mg/gm (dry weight).

36. A process according to claim 34, wherein the dried harvested plant contains combined amounts of 4-hydroxycinnamic acid and 4-hydroxy-3-methoxycinnamic acid totaling no more than 1.5 mg/gm (dry weight).

37. A process according to claim 34, wherein the harvested plant is immature corn, *Zea Mays*.

38. A process according to claim 37, wherein the immature corn has been grown to a height that does not exceed 30–45 centimeters.

39. A process according to claim 37, wherein the immature corn has been grown for no more than five weeks after planting.

40. A process according to claim 34, wherein the harvested plant is dried at a temperature in the rage of 40° C. to 45° C.

41. A process according to claim 31, wherein said chemical composition is administered in a manner selected from the group consisting of: (1) orally, in the form of tablets, capsules, suspensions, solutions and other means suitable for ingestion; (2) parenteral injection, in the form of subcutaneous, intramuscular, intravenous; (3) implant for sustained release; and (4) transdermal patch.

42. A process for treating mood disorders in humans by the administration of a therapeutically effective amount of one or more chemical compositions defined as:

Wherein "R" represents $C_1$–$C_4$ alkoxy, with stipulation that R is in the 4 or 5 ring position;

Wherein "n" represents one of the integers 0, 1 or 2; or pharmaceutically acceptable salts thereof.

43. A process according to claim 42, wherein one of said chemical compositions comprise 6-methoxy-2,3-benzoxazolinone defined as:

or pharmaceutically acceptable salts thereof.

44. A process according to claim 42, wherein the administered chemical composition comprises a daily dosage of 15 mg.

45. A process according to claim 42, wherein at least one of the chemical compositions is obtained from one or more monocotyledonous plants selected from the group consisting of corn, wheat, barley, rye, oats, rice, sorghum, millet, bamboo, barley-like grasses, and wild grasses, by growing the plant to an immature life history stage, harvesting the plant, and drying the harvested plant.

46. A process according to claim 45, wherein the harvested plant is dried at a temperature in the rage of 40° C. to 45° C.

47. A process according to claim 45, wherein the dried harvested plant contains phenols in total amounts greater than 17.0 mg/gm (dry weight).

48. A process according to claim 45, wherein the dried harvested plant contains combined amounts of 4-hydroxycinnamic acid and 4-hydroxy-3-methoxycinnamic acid totaling no more than 1.5 mg/gm (dry weight).

49. A process according to claim 45, wherein the harvested plant is immature corn, *Zea Mays*.

50. A process according to claim 49, wherein the immature corn has been grown to a height that does not exceed 30–45 centimeters.

51. A process according to claim 49, wherein the immature corn has been grown for no more than five weeks after planting.

52. A process according to claim 42, wherein said chemical composition is administered in a manner selected from the group consisting of: (1) orally, in the form of tablets, capsules, suspensions, solutions and other means suitable for ingestion; (2) parenteral injection, in the form of subcutaneous, intramuscular, intravenous; (3) implant for sustained release; and (4) transdermal patch.

* * * * *

UNITED STATES PATENT AND TRADEMARK OFFICE
CERTIFICATE OF CORRECTION

PATENT NO. : 6,667,308 B2
DATED : December 23, 2003
INVENTOR(S) : Rosenfeld et al.

It is certified that error appears in the above-identified patent and that said Letters Patent is hereby corrected as shown below:

Column 13,
Line 12, please delete "15", and insert therefor -- 16 --.

Column 14,
Line 5, please delete the following chemical structure:

and insert the following chemical structure therefor.

Line 20, please delete the following chemical structure:

and insert the following chemical structure therefor.

Signed and Sealed this

Ninth Day of November, 2004

*JON W. DUDAS*
*Director of the United States Patent and Trademark Office*